US011197939B2

(12) United States Patent
Borrego Castro

(10) Patent No.: US 11,197,939 B2
(45) Date of Patent: Dec. 14, 2021

(54) METHOD FOR CLEANING DISSOLUTION VESSELS AND SUBSEQUENT DOSING OF A DISSOLUTION MEDIA, AND MOBILE MODULAR CLEANING AND DOSING EQUIPMENT FOR THE IMPLEMENTATION THEREOF

(71) Applicant: Sotax AG, Aesch (CH)

(72) Inventor: Manuel Borrego Castro, Sabadell (ES)

(73) Assignee: Sotax AG, Aesch (CH)

( * ) Notice: Subject to any disclaimer, the term of this patent is extended or adjusted under 35 U.S.C. 154(b) by 633 days.

(21) Appl. No.: 14/895,498

(22) PCT Filed: Apr. 22, 2014

(86) PCT No.: PCT/ES2014/070345
§ 371 (c)(1),
(2) Date: Dec. 3, 2015

(87) PCT Pub. No.: WO2014/195543
PCT Pub. Date: Dec. 11, 2014

(65) Prior Publication Data
US 2016/0114064 A1    Apr. 28, 2016

(30) Foreign Application Priority Data

Jun. 3, 2013    (ES) ............................... ES201330809

(51) Int. Cl.
*A61L 2/07*        (2006.01)
*G01N 13/00*    (2006.01)
(Continued)

(52) U.S. Cl.
CPC .................. *A61L 2/07* (2013.01); *B01L 3/50* (2013.01); *B01L 13/02* (2019.08); *B08B 3/14* (2013.01);
(Continued)

(58) Field of Classification Search
None
See application file for complete search history.

(56) References Cited

U.S. PATENT DOCUMENTS

| 4,014,357 A * | 3/1977 | Sneed ....................... B08B 3/08 |
| | | 134/102.1 |
| 4,218,610 A * | 8/1980 | Baxter, Jr. ............. G01N 15/12 |
| | | 377/12 |

(Continued)

FOREIGN PATENT DOCUMENTS

| ES | 2393569 | 12/2012 |
| WO | WO 01/02095 | 1/2001 |

(Continued)

OTHER PUBLICATIONS

International Search Report dated Jul. 11, 2014 From the Oficina Espanola de Patentes y Marcas Re. Application No. PCT/ES2014/070345 and Its Translation Into English.

*Primary Examiner* — Mikhail Kornakov
*Assistant Examiner* — Pradhuman Parihar

(57) ABSTRACT

The invention relates to a method for cleaning dissolution vessels and for the subsequent dosing of a dissolution media, and to mobile modular cleaning and dosing equipment for the implementation of said method. According to said method, injected water steam is used for the cleaning and is subsequently aspirated, together with the residues of the dissolution, and the vessel is then refilled with the desired quantity of a new dissolution media. The mobile modular cleaning and dosing equipment allows the cleaning and dosing to be carried out in situ without having to remove the dissolution vessels from the equipment or site where the dissolution tests are carried out, using self-sufficient modular equipment, and a novel steam supply line is used for the
(Continued)

Figure 1:
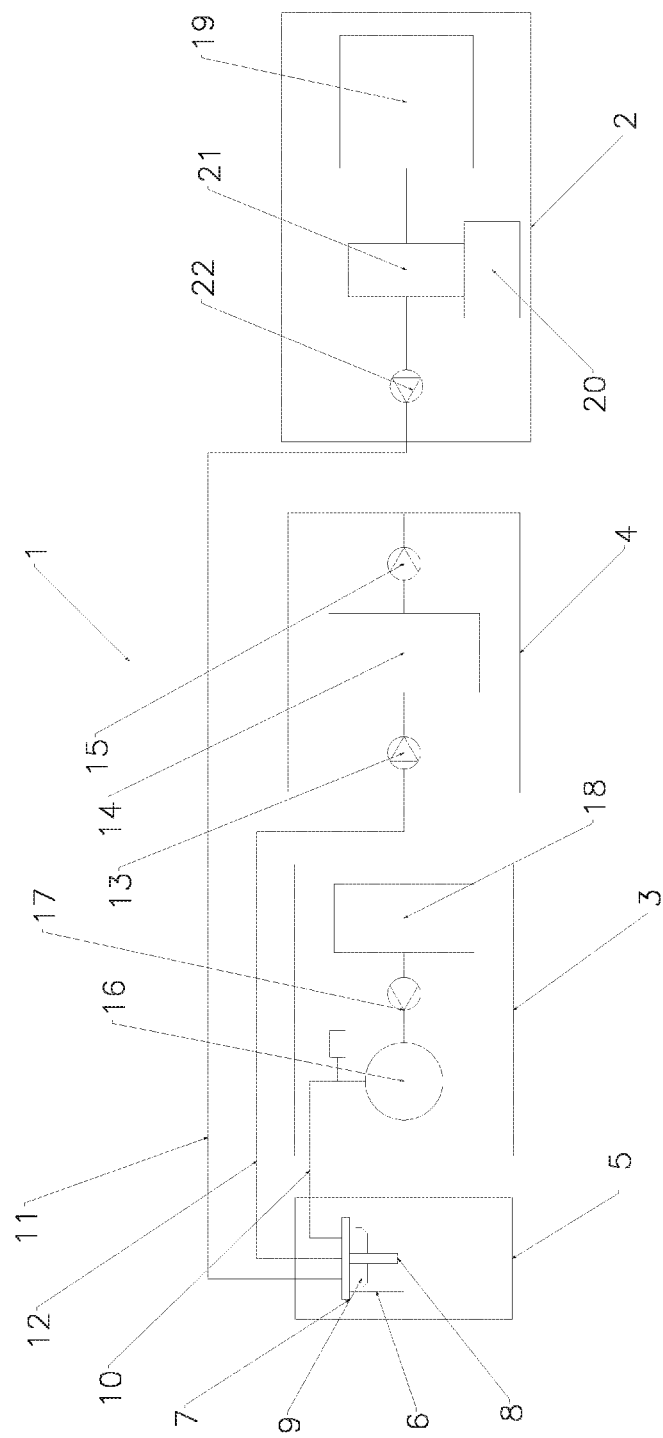

cleaning, which sprays the steam against the bottom of the vessel and the inner side walls.

4 Claims, 2 Drawing Sheets

(51) Int. Cl.
    *B01L 3/00*           (2006.01)
    *B08B 3/14*           (2006.01)
    *B08B 9/093*         (2006.01)
    *B08B 9/00*           (2006.01)

(52) U.S. Cl.
    CPC ............. *B08B 9/093* (2013.01); *G01N 13/00* (2013.01); *B01L 3/508* (2013.01); *B08B 9/00* (2013.01); *B08B 2230/01* (2013.01); *G01N 2013/006* (2013.01)

(56) References Cited

U.S. PATENT DOCUMENTS

| | | | |
|---|---|---|---|
| 4,318,885 A | | 3/1982 | Suzuki et al. |
| 4,635,665 A | * | 1/1987 | Namba ............... B08B 3/02 134/167 R |
| 6,026,837 A | * | 2/2000 | Chen ............... G05D 9/12 137/2 |
| 6,179,017 B1 | * | 1/2001 | Walter ............... B65B 39/12 134/166 C |
| 6,261,833 B1 | * | 7/2001 | de Oliveira ........... B01L 3/5082 422/412 |
| 2003/0198125 A1 | | 10/2003 | Linsen et al. |
| 2004/0115113 A1 | * | 6/2004 | Ohrem ............... C09K 5/063 423/395 |
| 2005/0074363 A1 | * | 4/2005 | Dunfee ............. G01N 35/1004 422/81 |
| 2007/0292309 A1 | * | 12/2007 | Lee ............... G01N 35/025 422/64 |
| 2008/0062522 A1 | * | 3/2008 | Britten ............... B08B 3/02 359/566 |
| 2010/0037919 A1 | | 2/2010 | Doebelin et al. |
| 2010/0047128 A1 | * | 2/2010 | Mototsu ............... B08B 3/02 422/63 |
| 2010/0126980 A1 | * | 5/2010 | Fetvedt ............... H05B 3/28 219/441 |
| 2012/0015862 A1 | * | 1/2012 | Travis ............... C11D 3/43 510/365 |
| 2012/0060446 A1 | * | 3/2012 | Merz ............... B65B 37/20 53/431 |
| 2012/0282153 A1 | * | 11/2012 | Cheong ............... F22B 1/282 422/292 |
| 2013/0025625 A1 | * | 1/2013 | Wochner ............... C01B 33/037 134/3 |
| 2013/0125673 A1 | * | 5/2013 | Kanipayor ............... G01N 1/42 73/863.11 |

FOREIGN PATENT DOCUMENTS

| | | |
|---|---|---|
| WO | WO 2008/055613 | 5/2008 |
| WO | WO 2014/195543 | 12/2014 |

\* cited by examiner

METHOD FOR CLEANING DISSOLUTION VESSELS AND SUBSEQUENT DOSING OF A DISSOLUTION MEDIA, AND MOBILE MODULAR CLEANING AND DOSING EQUIPMENT FOR THE IMPLEMENTATION THEREOF

RELATED APPLICATIONS

This application is a National Phase of PCT Patent Application No. PCT/ES2014/070345 having International filing date of Apr. 22, 2014, which claims the benefit of priority of Spanish Patent Application No. P201330809 filed on Jun. 3, 2013. The contents of the above applications are all incorporated by reference as if fully set forth herein in their entirety.

FIELD AND BACKGROUND OF THE INVENTION

The object of the present invention is to provide with a procedure or method for cleaning dissolution vessels using steam and the subsequent filling of said dissolution vessels with a dissolution media or solvent ready for use, the solvent, before being dosed, will be preheated and the appropriate amount will be measured. The mobile modular equipment for the implementation of the aforementioned method is also the object of the present invention.

Dissolution testing is becoming more and more common in the pharmaceutical industry. These tests determine the amount of active ingredient that is released into a certain dissolution media within an established timeframe and set temperature. The active ingredient is normally contained in a type of pharmaceutical formulation such as tablets, film-coated tablets, capsules or similar products used in therapeutic care.

The dissolution testing is carried out in a receptacle generally referred to as a dissolution vessel that contains a pre-set amount of dissolution media at a previously chosen temperature, usually 37 degrees, in which a dosing unit of the therapeutic agent that contains the active ingredient(s) is added and stirred. The samples of the dissolution are removed at pre-set time intervals and said samples are then analysed in suitable equipment in order to obtain the amount of the active ingredient that has been released into the dissolution media. When the testing is finished, the equipment must be cleaned to eliminate all trace or residue of the dissolution in order to move onto a new test of the same therapeutic agent or a different one.

The foregoing method may be performed manually or using equipment with a greater or lesser level of automation.

According to the state of the art, the washing or cleaning of dissolution vessels is performed using liquids that are subsequently aspirated and brushes are occasionally used to obtain the desired results.

The proposed invention offers a method for cleaning dissolution vessels using pressurised water steam and their subsequent filling with a new dissolution media and mobile equipment to carry out the method for one or more dissolution vessels without having to remove them from their housing in the dissolution equipment and without using equipment that consumes a large amount of water and time in cleaning and subsequently conditioning the dissolution vessels.

SUMMARY OF THE INVENTION

The proposed method for cleaning dissolution vessels and subsequent dosing of the dissolution media comprises the following stages:

A. General conditioning, which in turn comprises the successive or simultaneous sub-stages:
   a. Generating water steam.
   b. Preheating the dissolution media to be dosed.
   c. Emptying the waste tank and optional insertion of neutralizing or anti-foam solution into said waste tank.

B. Cleaning the dissolution vessel, which in turn comprises the following successive or simultaneous sub-stages:
   a. Fitting and adjusting the cover of the dissolution vessel.
   b. Pressing the button to start the process.
   c. Aspiration of the dissolution media using the aspiration tube.
   d. Transferring into the waste tank.
   e. Optionally adding one or more chemical additives to water steam.
   f. Injection of water steam at predetermined temperatures and pressure levels for a given time period depending on the dissolution media used and the therapeutic agent tested
   g. Aspiration of steam using the aspiration tube and transferring into the waste tank.
   h. Transferring the dissolution media and steam contained in the waste tank to the outside.

C. Dosing, which in turn comprises the successive or simultaneous sub-stages:
   a. Transferring the preheated dissolution media from the storage deposit into the dosing deposit.
   b. Measuring the predetermined amount of dissolution media to be dosed using a gravimetric measuring device.
   c. Transferring the dissolution media into the dissolution vessel.

Whereby, stage B, cleaning the dissolution vessel, and stage C, dosing, are consecutive and independent of each other and that in the procedure described above, stage B is compulsory, since during the dissolution testing, the final stage is to leave the already used dissolution vessels ready for carrying out new tests, which may be required after a certain time has elapsed, and stage C which is an optional part of the procedure.

The modular cleaning and dosing equipment for the implementation of the aforementioned method comprises the following modules, provided in FIG. 1:

A. Cover module, which in turn comprises a cover consisting of a piece manufactured from plastic with coupling and seal-tight adjustment means, preferably of the sealing gasket type, at the top of the dissolution vessel; a vacuum breaker system conveniently arranged in the cover, preferably of the hole type, which enables the insertion of a plastic filter, preferably a 35 micron mesh made of PVDF (polyvinycoverene difluoride); a aspiration tube of variable length, manufactured from a plastic material, in order to be used in different sized dissolution vessels, coupled in a seal-tight manner to the cover and connected to the aspiration line of the dissolution media; a check valve, preferably of the ball and spring type, suitably arranged in the aspiration tube in order to prevent the dissolution media that has been aspirated accidently returning to the dissolution vessel; a particle filter suitably arranged in said aspiration tube, preferably a mesh manufactured from stainless steel; a supply line for steam connected to a steam distributor that consists of a piece made from plastic, preferably PTFE (polytetrafluorethylene), with upper seals ideally manufactured by Viton, a registered brand of fluoroelastomer, an inner channel for the circulation of steam and a series of holes arranged perpendicularly to the channel with outer opening so that the steam can be radially supplied against the inner walls of the dissolution vessel; a supply line for the dissolution media and an activation switch to give the command to the control module to start or stop the process.

B. Aspiration module for the dissolution media and steam that comprises an aspiration system, preferably a aspiration pump with a sealing gasket, connected to a waste tank for the storage of already used dissolution media and steam, equipped with level sensors and draining pump for the same with check valves and their corresponding interconnection and connection piping and fittings to enable connection with other modules.

C. Water Steam generation module that comprises a boiler manufactured from stainless steel duly equipped with one or more electrical heaters, water level sensors, safety thermostat, pressure/temperature control system, preferably but not limited to, via pressure switch, solenoid valve, safety valve, vacuum breaker system, preferably of the vent valve type, filling pump for the boiler with its corresponding check valve, water supply tank for the boiler with level sensors, as well as their corresponding interconnection and connection piping and fittings to connect the rest of the modules, and, as an optional design element, a device for adding chemical additives to the supply line of the generated steam.

D. Dosing module for the dissolution media that contains a storage deposit for the dissolution media with level sensors and heating system with temperature control, preferably one or more electrical heaters with thermostats; gravimetric measuring device for the dissolution media to be supplied, preferably using gravimetric load cells; dosing deposit that contains the amount of dissolution media to be supplied into the dissolution vessel incorporating a vacuum breaker system, preferably of the vent valve type; a drive system for the dissolution media for dosing, and their corresponding tubing, fittings and solenoid for interconnecting and connecting the rest of the modules, E. Control module with an information screen and data input that controls, at least, the activation of the switch for the cover module, the water steam pressure, the injection time for the steam in the dissolution vessel, the time and cycles to aspirate the dissolution media, the temperature and amount of the dissolution media to be dosed, and, optionally, the amount of chemical additive to be added to the water steam to be supplied F. Transportation module that comprises a frame to which the rest of the modules are coupled, and on which transportation means are suitably arranged, preferably groups of one or more wheels.

As a design option, the different modules that comprise the invention may be separated from each other or grouped in different module combinations, each module or group of modules being provided with its corresponding frame and transport means, preferably in groups of one or more wheels.

BRIEF DESCRIPTION OF THE SEVERAL
VIEWS OF THE DRAWINGS

Figure 2:
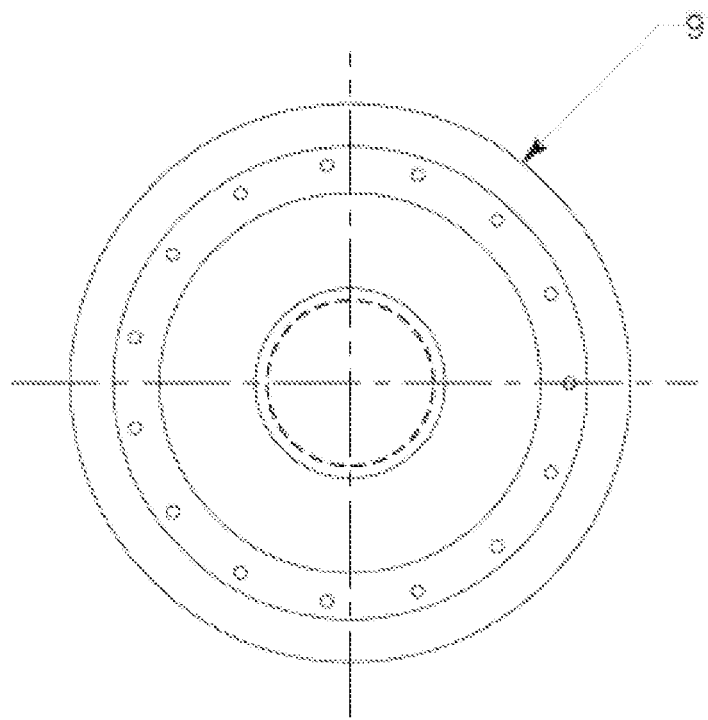
Figure 2:
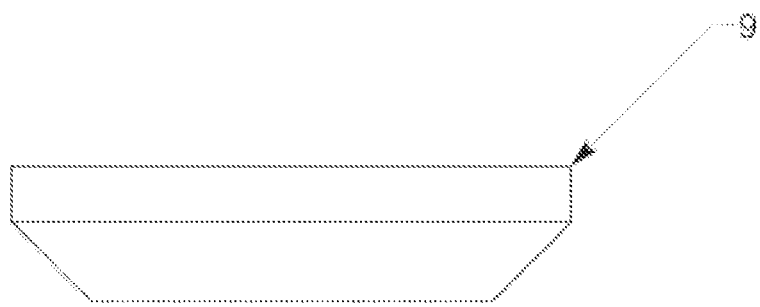

FIG. 1: diagram of the modular equipment
FIG. 2 *a*: top view of the steam distributor
FIG. 2 *b*: side view of the steam distributor

LIST OF REFERENCES

1. Modular cleaning and dosing equipment for dissolution vessels.
2. Dosing module
3. Steam generation module
4. Aspiration module
5. Cover module
6. Dissolution vessel
7. Cover
8. Aspiration tube
9. Steam distributor
10. Steam supply line
11. Dissolution media supply line
12. Aspiration line
13. Aspiration pump
14. Waste tank
15. Draining pump
16. Boiler
17. Filling pump
18. Supply deposit to the boiler
19. Dissolution media deposit
20. Gravimetric measuring device
21. Dosing deposit
22. Dosing pump

DESCRIPTION OF SPECIFIC EMBODIMENTS
OF THE INVENTION

FIG. 1 shows a preferred embodiment of the mobile modular equipment for cleaning and dosing dissolution vessels in which the aspiration module and water steam generation module are joined to the same assembly and separated from the dosing and cover modules. In this embodiment, the module interconnection tubing, along with quick coupling fittings and wheeled transport means for the module assembly are conveniently arranged.

This equipment requires general conditioning prior to the start of the cleaning and dosing method, consisting of the preparing steam via the supply of water to the boiler from the filling deposit using the filling pump; heating, preferably using electrical heater, the water until evaporation and overheating up to reach a minimum pressure level indicated by the sensor; and optionally, introducing a neutralizer/anti-foam solution to condition the dissolution media to be aspirated inside of the waste tank. Likewise, the dissolution media to be dosed must preferably be preheated using electrical heater to the pre-set temperature.

The washing and dosing method in this embodiment are carried out independently of each other.

The method begins with the placement of the cover in the top of the dissolution vessel and then actuating the manual switch to indicate to the control module to start the process.

The washing method necessarily implies aspiration of the dissolution media present in the dissolution vessel through the aspiration tube and transferring it into the waste tank, preferably being introduced through the bottom of the same, which is mixed with the media present in the tank and, optionally, with the neutralizing and/or anti-foam solution previously added during the conditioning stage.

After the washing thereof, steam from the boiler is added to the dissolution vessel through the steam line connected to the steam distributor, FIGS. 2*a* and 2*b*, which enables it to be radially and symmetrically projected onto the inner walls of the vessel so that it may be cleaned better. The steam is aspirated using the aspiration tube and taken to the waste tank via the aspiration line, such that the cleaning process has been carried out.

When the level of the waste tank exceeds a limit predetermined by the maximum level sensor, the waste tank, through the draining pump, expels the already used dissolution media, sending it to the suitable storage and waste treatment devices. The end of the draining process is determined using a minimum level sensor of the waste tank.

When the water level in the boiler exceeds the pre-set lower limit, the filling pump of the boiler will replace the water and start the conditioning process once again The method for dosing the dissolution media begins with transferring the pre-set amount of the media, previously heated in the conditioning process, to the dosing deposit, preferably determined by gravimetric load cell measurement devices, said transferring to the dissolution vessel is performed using the dosing pump.

When the level of the dissolution media present in the media tank exceeds a predetermined lower limit, it will be necessary to replace the dissolution media and begin the conditioning process once again.

The details, shapes, dimensions and other accessory elements, as well as the materials used to manufacture the tools of the invention may be conveniently replaced with others that are technically equivalent and do not depart from the essence of or the scope defined in the claims included below:

What is claimed is:

1. A method for cleaning a dissolution vessel and subsequent dosing of a dissolution medium with a cleaning and dosing apparatus, comprising:
    fitting an adjustable cover over an opening of the dissolution vessel, wherein an aspiration tube is mechanically coupled to an outlet orifice of the cover, a dissolution media supply line is mechanically coupled to a first inlet orifice of the cover, and a steam supply line is mechanically coupled to a second inlet orifice of the cover, and wherein the aspiration tube, the dissolution media supply line and the steam supply line are mechanically coupled to the cover in a seal-tight manner;
    operating, with a control unit of the apparatus, at least one aspiration pump to suck used dissolution medium contained in the dissolution vessel, wherein the used dissolution medium is sucked through the aspiration tube, and wherein the used dissolution medium is transferred through an aspiration line into a waste tank;
    operating, with the control unit, at least one steam distributor to inject heated steam into the dissolution vessel through the steam supply line;
    operating, with the control unit, the at least one aspiration pump to suck the steam from the dissolution vessel through the aspiration tube, wherein the steam is transferred through the aspiration line into the waste tank;
    operating, with the control unit, at least one dosing pump to transfer a predefined amount of unused dissolution medium from a dissolution medium deposit to a dosing deposit, the predefined amount of the unused dissolution medium is determined using a gravimetric measuring device, wherein the unused dissolution medium had been preheated by a heating system of the apparatus; and
    operating, with the control unit, the at least one dosing pump to transfer the predefined amount of unused dissolution medium from the dosing deposit to the dissolution vessel through the dissolution medium supply line,
    wherein the at least one steam distributor is positioned inside the dissolution vessel and connected to the steam supply line through said second inlet orifice, the at least one steam distributor comprises upper seals, an inner channel for the circulation of steam and a plurality of holes arranged perpendicularly to the channel with outer opening so that the steam is radially supplied against inner walls of the dissolution vessel; and
    wherein the dissolution vessel is configured within a housing in the dosing and cleaning apparatus and retained stationary in the housing throughout the fitting step and each of the operating steps.

2. The method according to claim 1, further comprising adding a neutralizing solution to the waste tank after the waste tank is emptied in order to condition the used dissolution medium transferred into the waste tank.

3. The method according to claim 1, further comprising adding an anti-foam solution to the waste tank in order to condition the used dissolution medium transferred into the waste tank.

4. The method according to claim 1, further comprising adding one or more chemical additives to the steam injected into the dissolution vessel.

* * * * *

UNITED STATES PATENT AND TRADEMARK OFFICE
CERTIFICATE OF CORRECTION

| | |
|---|---|
| PATENT NO. | : 11,197,939 B2 |
| APPLICATION NO. | : 14/895498 |
| DATED | : December 14, 2021 |
| INVENTOR(S) | : Manuel Borrego Castro |

It is certified that error appears in the above-identified patent and that said Letters Patent is hereby corrected as shown below:

On the Title Page

Item (30) Foreign Application Priority Data, "ES201330809" should be changed to -- P201330809 --

Signed and Sealed this
Third Day of May, 2022

Katherine Kelly Vidal
*Director of the United States Patent and Trademark Office*